United States Patent [19]
Enriquez et al.

[11] Patent Number: 5,490,991
[45] Date of Patent: Feb. 13, 1996

[54] DIRECTED DELIVERY OF RADIOPROTECTANTS USING A RECEPTOR SPECIFIC CARRIER

[75] Inventors: Philip Enriquez, Sheldonville; Chu W. Jung, Arlington; Ernest V. Groman, Brookline, all of Mass.

[73] Assignee: Advanced Magnetics, Inc., Cambridge, Mass.

[21] Appl. No.: 43,611

[22] Filed: Apr. 5, 1993

Related U.S. Application Data

[63] Continuation-in-part of Ser. No. 900,686, Jun. 17, 1992, which is a continuation-in-part of Ser. No. 938,873, Aug. 27, 1992, Pat. No. 5,336,506, which is a continuation of Ser. No. 630,017, Dec. 19, 1990, abandoned, which is a continuation-in-part of Ser. No. 679,526, Apr. 2, 1991, Pat. No. 5,141,739, which is a continuation of Ser. No. 384,991, Jul. 28, 1989, abandoned, which is a continuation of Ser. No. 228,640, Aug. 4, 1988, abandoned, which is a continuation-in-part of Ser. No. 76,586, Jun. 26, 1987, Pat. No. 4,827,945, which is a continuation-in-part of Ser. No. 882,044, Jun. 13, 1985, Pat. No. 4,698,302.

[51] Int. Cl.$^6$ .................................................... A61K 9/127
[52] U.S. Cl. .......................... 424/488; 424/484; 424/450
[58] Field of Search ................................ 424/450, 488, 424/484; 435/173; 530/810; 514/777

[56] References Cited

U.S. PATENT DOCUMENTS

| | | | |
|---|---|---|---|
| 4,946,830 | 8/1990 | Pulverer | 514/23 |
| 5,096,708 | 3/1992 | Gohla et al. | 424/195 |
| 5,284,646 | 2/1994 | Menz | 424/9 |

FOREIGN PATENT DOCUMENTS

| | | |
|---|---|---|
| 3042491 | of 0000 | Germany. |
| 87/07150 | of 0000 | WIPO. |
| 90/01295 | of 0000 | WIPO. |

OTHER PUBLICATIONS

Bodmer Methods in Enzymology 112, p. 298, 1985.
Duncan, Marcel Dekkar, p. 581, 1987.
Dragstein BBA 926, p. 270 (1987).
Stockert Can. Res. 40, 3632, 1980.
Stahl et al., "Receptor–Mediated Pinocytosis of Mannose Glycoconjugates by Macrophages: Characterization and Evidence for Receptor Recycling," Cell 19:207–215 (1980).
Stockert et al., "Diminished Hepatic Binding Protein for Desialylated Glycoproteins During Chemical Hepatocarcinogensis," Cancer Research 40:3632–3634 (1980).
Regoeczi et al., "Galactose–Specific Elimination of Human Asialotransferrin by the Bone Marrow in the Rabbit," Arch. Biochem. Biophys. 205:76–84 (1980).
Schwartz et al., "Characterization of the Asialoglycoprotein Receptor in a Continuous Hepatoma Line," J. Biol. Chem. 256:8878–8881 (1981).
Shen et al., "CIS–Aconityl Spacer Between Daunomycin and Macromolecular Carriers: A Model of pH–Sensitive Linkage Releasing Drug from a Lysosomotropic Conjugate," Biochem. & Biophys. Res. Comm. 102:1048–1054 (1981).
Rodewald et al., "Receptor–Mediated Transport of IgG," J. Cell. Biol. 99:159s–164s (1984).
Samlowski et al., "Bone Mararow Engraftment Efficiency is Enhanced by Competitive Inhibition of the

(List continued on next page.)

Primary Examiner—Gollamudi S. Kishore
Attorney, Agent, or Firm—Bromberg & Sunstein

[57] ABSTRACT

Chemoactive radioprotectants are coupled to carrier molecules capable of binding cell receptors to form complexes that can be directed to specific non-target cells in a mixture of cells prior to radiation of the mixture so that target cells are selectively destroyed while the non-target cells are protected from radiation. Radioprotection of non-target cells is provided by using chemoactive radioprotectant complexes.

12 Claims, 2 Drawing Sheets

OTHER PUBLICATIONS

Hepatic Asialogycoprotein Receptor," Proc. Natl. Acad. Sci. USA 82:2501–2512 (1985)

Fahey et al., "Measurement of WR–2721, WR–1065, and WR–33278 in Plasma," Int. J. Radiation Oncology Biol. Phys. 11:1193–1197 (1985).

Samlowski, et al., "Characterization of the in Vitro Interaction of PNA$^{hi}$ Lymphocytes with the Bone Marrow and Hepatic Asialoblycoprotein Receptors," Cellular Immunology 95:1–14 (1985).

Wileman et al., "Receptor–Mediated Endocytosis," Biochem. J. 232:1–14 (1985).

Neutra et al., "Intracellular Transport of Transferrin—and Asialoorosomucoid–Colloidal Gold Conjugates to Lysosomes after Receptor–Mediated Endocytosis," J. Histochem. & Cytochem. 33:1134–1144 (1985).

Taylor et al., "Mammalian Mannose–Binding Proteins," Clin. Sci. 70:539–546 (1986).

Wileman et al., "Identification of the Macrophage Mannose Receptor as 175–kDa Membrane Protein," Proc. Natl. Acad. Sci. USA 83:2501–2505 (1986).

Lightdale et al., "Management of Primary and Metastatic Cancer of the Liver," Diseases of the Liver, Schiff et al. Eds., Phila.: J. B. Lippincott Company, 1987, pp. 1159–1170.

Ward, J. H., "The Structure, Function, and Regulation of Transferrin Receptors," Invest. Radiol. 22:74–83 (1987).

Livesey et al., "Chemical Protection Against Ionizing Radiation," Advances in Radiation Biology 13:285–351 (1987).

Rasey et al., "Specific Protection of Different Normal Tissues," Pharmac. Ther. 39:33–43 (1988).

Stratford et al., "Studies on the Role of Antioxidants in Radioprotection," Pharmac. Ther. 39:389–391 (1988).

Wanebo et al., "Cancer of the Hepatobiliary System," Cancer: Principles & Practice of Oncology 3rd Edition, DeVita et al. Eds., Phila.: J. B. Lippincott Company, 1989, pp. 836–874.

Coleman et al., "Chemical Modification of Radiation and Chemotherapy," Cancer: Principles & Practice of Oncology 3rd Edition, DeVita et al. Eds., Phila.: J. B. Lippincott Company, 1989, pp. 2436–2447.

Kemeny et al., "Treatment of Metastatic Cancer to Liver," Cancer: Principles & Practice of Oncology 3rd Edition, DeVita et al. Eds., Phila.: J. B. Lippincott Company, 1989, pp. 2275–2298.

Moss et al., Radiation Oncology, St. Louis: The C. V. Mosby Company, 1989, pp. 1–57.

Magnusson et al., "Extremely Rapid Endocytosis Mediated by the Mannose Receptor of Sinusoidal Endothelial Rat Liver Cells," Biochem. J. 257:651–656 (1989).

Ono et al., "Frequency of Micronuclei in Hepatocytes Folowing X and Fast–Neutron Irradiations—An Analysis by a Linear–Quadratic Model," Radiation Research 347 (1990).

Ezekowitz et al., "Molecular Characterization of the Human Macrophage Mannose Receptor: Demonstration of Multiple Carbohydrate Recognition–like Domains and Phagocytosis of Yeasts in Cos–1 Cells," J. Exp. Med. 172:1785–1794 (1990).

Patchen et al., "Postirridation Treatment with Granulocyte Colony–Stimulating Factor Comgined with Preirradiation Treattment with WR–2721 Synergize to Enhance Hemopoietic Reconstitution and to Increase Survival," 7th International Conference on Chemical Modifiers of Cancer Treatment, pp. 324–325 (Feb. 2–5, 1991).

Jansen et al., "Hepatic Endocytosis of Various Types of Mannose–Terminated Albumins," J. Biol. Chem. 266(5):3343–3348 (1991).

Meijer et al., "Drug Targeting Systems for Antiviral Agents; Options and Limitations," Antiviral Research 18:215–258 (1992).

Van der Sluijs et al., "Limitations on the specificity of Targeting Asialoglycoprotein–Drug Conjugates to Hepatocytes" pp. 235–264 in Liver Diseases: Targeted Diagnosis and Therapy using Specific Receptors and Ligands ed Wu and Wu pub. Marcel Dekker Inc. (1991).

WR 1065 (R = —H) and
WR 2721 (R = —PO$_3$H$^-$)

R—S—CH$_2$CH$_2$—NH—CH$_2$CH$_2$CH$_2$—NH$_2$

Vitamin E

LEGEND:

LINOLEIC ACID

VITAMIN E

TWEEN 80

AG-AMINE

FIG. 3

DIRECTED DELIVERY OF RADIOPROTECTANTS USING A RECEPTOR SPECIFIC CARRIER

CROSS REFERENCES TO RELATED APPLICATIONS

This application is a continuation-in-part of application Ser. No. 900,686, filed Jun. 17, 1992 which is a continuation-in-part of application Ser. No. 938,873, filed Aug. 27, 1992, now U.S. Pat. No. 5,336,506, which is a continuation of Ser. No. 630,017, filed Dec. 19, 1990, now abandoned, which is a continuation in part of Ser. No. 679,526 filed Apr. 2, 1991, now U.S. Pat. No. 5,141,739, which is a continuation of Ser. No. 384,991, filed Jul. 28, 1989, now abandoned, which is a continuation in part of Ser. No. 228,640 filed Aug. 4, 1988, now abandoned, which is a continuation In part of Ser. No. 076,586, filed Jun. 26, 1987, now U.S. Pat. No. 4,827,945, which is a continuation in part of Ser. No. 882,044, filed Jun. 13, 1985, now U.S. Pat. No. 4,698, 302, all of which are incorporated herein by reference.

TECHNICAL DESCRIPTION

The present invention relates to methods of treating cells, tissues, and organs by directing the delivery of radioprotectants and compositions containing such agents to them prior to the administration of radiation treatment.

BACKGROUND OF THE INVENTION

Radiation treatment has been used for treating patients with cancer for almost 100 years.

A. Problems with Radiation Therapy

Today, radiation treatment is commonly used as a form of therapy for treating primary and metastatic tumors. Typically, a radiation beam is focused at a finite number of known or suspected tumors with the radiation doses and path of radiation designed to minimize damage to surrounding, non-target, normal cells. Obviously, for beam focused radiation therapy to be successful, the location of a finite number of tumors must be known. For example, beam focused radiation for the treatment of primary or metastatic cancer of the liver is hampered by diffuse infiltration of the liver by secondary or primary liver cancer. In addition, the liver is a tissue that is sensitive to radiation, see below.

A second type of radiation therapy involves non-selective whole body treatment with high doses of irradiation. In this type of therapy, bone marrow is removed prior to irradiation to avoid irradiation of the stem cells. (The bone marrow stem cells give rise to the cells of immune and blood systems). The patient then undergoes whole body irradiation, which kills both cancer cells, whose location may or may not be known, and also kills cells of the blood and immune system. While the patient is being irradiated, the bone marrow is purged of contaminating cancer cells, by one of a variety of techniques. The purged marrow is replaced into the patient after radiation has been completed. The purging of marrow and replacement in the patient is sometimes called autologous bone marrow transplantation. In autologous bone marrow transplantation, radiation is used non-selectively, on the whole body, the selective non-irradiation of the stem cells being accomplished by physical removal of those cells from the patient. Autologous bone marrow transplantation is expensive and risky because the patient lacks an immune system until the replaced bone marrow begins to proliferate and yields functioning blood and immune cells. Currently, autologous bone marrow transplantation is used only in hematological cancers that have not responded to standard forms of chemotherapy. Thus, radiation therapy is either tumor specific by virtue of the path of the radiation beam(s), or selective by virtue of the removal of stem cells.

B. Chemistry of Radiation Damage

Radiation disrupts cells by fatally altering the genetic and somatic functions of cellular constituents. DNA is particularly sensitive to radiation. Damage to DNA occurs either by direct radiation or by reaction with hydroxyl radicals produced from radiolysis of neighboring water molecules. Reaction with oxygen produces peroxyl radical $DNA-O_2$ which forms products that cause irreversible damage to the DNA unless counteracted with reducing species such as a thiol to restore the original molecule (Coleman, in: Cancer, Principles and Practice of Oncology, 3rd Ed., DeVita et al., Eds., Phila.: JB Lippincott Co., 1989). Consequently thiols have an established radioprotective activity. Because of the central role oxygen is believed to play in radiation damage, the cells most vulnerable to radiation are those that are well oxygenated and are dividing. These include stem cells (bone marrow cells) and cells that are highly perfused with oxygen, for example, liver cells, endothelial cells and epithelial cells in the lung. In some cases the sensitivity of normal cells to relatively low radiation doses is great, and the adverse effects caused by radiation of non-target cells may offset any advantage accrued from reducing the tumor load.

C. Sensitivity of the Liver to Radiation

The treatment of liver cancer with radiation both embodies many of the problems of radiation therapy and is a specific embodiment of the current invention.

At the time of detection of primary or secondary cancer within the liver, there are often multiple tumors within the liver that prevent surgical resection. In the extreme case, the cancer can be diffuse, or exist not as discrete tumors, but intermixed with normal tissue throughout the liver. Radiation therapy is hampered by the liver's inherent sensitivity to radiation.

In the liver approximately 5,000 rads is considered necessary to achieve a high probability of control over a subclinical adenocarcinoma (i.e., <$10^6$ cells), and 6,000 rads to control a squamous cell tumor of less than 2 cm (Hall et al. in: Radiation and Oncology Rationale, Moss et al. Eds., 1989, pp. 1–57). However, the liver has a low radiation tolerance (2500–3000 rad), and radiation doses of more than 3,000 rad within 3 weeks can result in radiation hepatitis (Wanebo et al. In: Cancer Principles and Practice of Oncology. Hellman et al. Eds., Phila.: JB Lippincott, 1989, pp. 836–874). To treat liver tumors successfully with radiation there is a need to develop a method of treatment that spares the hepatocytes while increasing the damage to tumors (Ono et al. in: Radiation Research, 1990, 123:345–347.

D. Pharmaceutical Agents Used to Alter Effects of Radiation

Attempts to use pharmaceutical agents in conjunction with radiation for the treatment of cancer have often involved two general approaches: (1) lowering the radiation tolerance of the tumor, i.e., making the tumor more susceptible to radiation; and (2) raising the radiation tolerance of non-target cells by protecting them from or reducing the damage to them during radiation therapy. For the former method, compounds such as hypoxic cell sensitizers are administered on the theory that hypoxic cells, such as tumor cells, are less sensitive to radiation (Coleman, in: Cancer, Principles and Practice of Oncology, 3rd Ed., DeVita et al., Eds. Phila.: JB Lippincott Co., 1989, pg. 2436). The latter form of radioprotection attempts to eliminate or minimize the effects of radiation on non-target tissue. Radioprotecting agents can be classified as falling into two general types. They are biologically active radioprotective agents and chemoactive radioprotective agents.

1. Biologically Active Radioprotective Agents

Some agents are radioprotective because they possess a biological activity which, after radiation, ameliorates or compensates for the damage produced by radiation. Their indirect radioprotecting capability stems from the abilities of the agents to modify biological responses, such as to suppress or stimulate the immune systems, or initiate or accelerate repair of damaged tissue. Molecules that stimulate repair or replacement of damaged cells include certain hormones and hormone-like compounds, immuno-potentiators, immuno-stimulators and anti-inflammatory agents. Gohla (U.S. Pat. No. 5,096,708) disclosed that an active component derived from Thuja occidentalis that contains polysaccharides acts as an immune-stimulant assisting the reconstitution of bone marrow cells after radiation damage has occurred. Similarly, Wagner et al. (DE 3,042,491) report that infections which arise in a person after radiation damage can be effectively prevented or controlled by a polysaccharide derived from a plant of the compositae family that acts as an immune stimulant.

Another approach to protecting non-target cells from radiation is to inhibit their growth and differentiation. Keller et al. (U.S. patent application Ser. No. 7,372,815) used antibodies to transforming growth factor-beta-1 to inhibit hematopoietic progenitor growth and differentiation prior to radiation and thereby reduce susceptibility of these cells to radiation damage, an effect that is greatest in dividing cells.

2. Chemoactive Radioprotective Compounds

Chemoactive radioprotectants compounds (CRC's) are agents which directly protect cells from radiation damage. Examples of chemoactive radioprotective agents include low molecular weight compounds such as free radical scavengers or anti-oxidants (vitamin E, ascorbic acid). Sulfhydryl compounds (compounds containing an SH-group) and cationic thiols (sulfhydryl compounds containing an amine group), function as free radical scavengers, and accordingly have been evaluated for use as chemoactive radioprotectants. Examples of cationic thiols that act as protective agents are S-2-(3-aminopropylamino) ethyl phosphophorothioic acid (WR2721), a thiophosphate derivative of aminothiol cysteamine and 2-(3-aminopropyl) aminoethanethiol (WR1065). Some CRC's are high molecular weight molecules. These include biological molecules that have anti-oxidant properties such as the enzyme superoxide dismutase, which destroys the oxygen anion (superoxide) generated during radiation and reduces the concentrations of mediators of radiation damage. Other radioprotectant agents include selenium, melanins, cysteamine derivatives, phenolic functional groups (such as 6-hydroxy-chroman-2 carboxylic acids (e.g., Trolox®) and tocopherols (e.g., Vitamin E), and enzymes (superoxide dismutase). Table 1 lists selected CRC's.

Current CRC's suffer from the following limitations:

1. Low molecular weight CRC's are rapidly excreted by glomerular filtration of the blood through the kidney. This limits both the uptake of the CRC by normal tissue and the time the CRC is in the body.

2. The ability of CRC's that are macromolecular (high molecular weight) to protect against radiation damage is limited because macromolecules do not cross membranes surrounding cells. They do not enter the cytoplasm and are confined to a location far from the DNA molecules that need their protection.

3. Both high and low molecular weight CRC's lack cell or organ selectivity. For example, plasma distributes low molecular weight thiols throughout the extracellular fluid around cells as well as within cells in the intracellular fluid. To achieve concentrations sufficient for the radioprotection of any particular cell or tissue, high concentrations of CRCs must be achieved in all cells. This lack of selectivity increases the dose of agent that must be administered and increases the possibility of toxic reactions to the agent.

4. Both high and low molecular weight CRC's lack adequate selectivity for normal tissue over tumor tissue. Probably the best known CRC is S-2-(3-aminopropylamino) ethylphosphorothioic acid, a thiophosphate derivative of aminothiol cysteamine known as WR2721. Developed earlier as a protective agent for battlefield radiation, WR 2721 has been the subject of recent clinical investigations. The major obstacle to the use of WR2721 in radiotherapy of liver cancer is its non-selectivity, which resulted in the rejection of WR2721 as a protecting agent (The Pink Sheet, Feb 3, 54, #5 (1992)).

SUMMARY OF THE INVENTION

For the foregoing reasons there is a need for a class of new radioprotectants that can be (i) efficiently directed to a particular population of cells or a particular tissue and (ii) selectively protect non-target cells and tissues and not protect tumor cells. This invention satisfies the need for radioprotectants that can be directed to a specific population of non-target cells in different organs or tissues.

The current invention is a method for radiating a mixture of cells so as to destroy target cells while protecting specific non-target cells in the mixture against radiation damage. In one embodiment, a radioprotectant compound (CRC) is selected and a complex is formed with a carrier, that carrier being capable of binding to a receptor on non-target cells. The complex is then administered to the mixture of cells thereby providing protection during radiation of the mixture of cells at doses sufficient to destroy target cells.

In another embodiment, a method of treating animal subjects (where animal subjects include humans) with radiation is provided, where these subjects have diffuse cancerous infiltrations. A carrier capable of interacting with a cell receptor is selected, and subsequently modified to form a complex with a radioprotectant. The complex is then administered at an effective dose so as to protect non-target cells during subsequent radiation of tissues at doses sufficient to destroy malignant cells.

In another embodiment, a radioprotectant-carrier complex including a radioprotectant compound, a carrier and a vehicle is assembled in a complex where the radioprotectant agent is conjugated to the carrier and the complex is capable of binding to cell receptors on selected cells, the complex having a specificity for those cell receptors located on the non-target cells.

In a further embodiment, a micelle composition comprises a core of radioprotectant molecules, the radioprotectant molecules being surrounded by a lipid shell and the lipid shell being associated with a carrier molecule wherein the associated carrier is suitable for selectively delivering the micelle to normal non-target tissue so as to provide radioprotection of non-target cells during radiation of a mixture of cells, the mixture including target and non-target cells.

BRIEF DESCRIPTION OF THE DRAWINGS

These and other features, aspects and advantages of the present invention will become better understood with reference to the following description, appended claims, and accompanying drawings where:

DETAILED DESCRIPTION OF SPECIFIC EMBODIMENTS

Before discussing the invention in detail, certain terms are here defined for the purposes of this description and the following claims.

"Target cells" are cancer cells whose destruction by radiation is desirable.

"Non-target cells" are non-malignant cells whose destruction by radiation is undesirable or harmful. These cells are usually normal cells either surrounding the target cells or cells in the path of radiation.

"Chemoactive radioprotecting compounds" (CRC's) are compounds capable of protecting cells, tissues, or organs from the damaging effects of radiation.

"Carriers" are molecules capable of binding to a receptor including receptors that perform receptor mediated endocytosis (RME).

"Directed delivery" of a CRC occurs when the CRC is attached to a carrier, becomes bound to a receptor and may be taken up by cells at the site of binding.

There has been a longstanding interest in the changes in cell surface membranes that may occur in the conversion of normal cells to malignant cells. It has been noted that these changes include loss of membrane receptors and that this loss is characteristic of carcinogenic evolution. In addition, these changes may serve as histochemical markers for identifying premalignant cells (Stockert et al., Cancer Res. 1980, 40:3632). The invention described herein exploits differences in receptor properties between normal and malignant cells for a novel and different purpose to that described by Stockert et al. Differences in receptor properties between normal and malignant cells have here been used to deliver radioprotectants to non-malignant cells so as to protect the cells from the lethal effects of radiation.

One family of receptors that are found on normal cells and occur in greatly reduced numbers on cancer cells are RME-type receptors. An example of an RME-type receptor is the asialoglycoprotein receptor, a relatively abundant protein on the surface of cells. Variants of this receptor are found on both bone marrow cells (Regoeczi et al., Arch. Biochem. Biophys., 1980, 205:76; Samlowski et al., Proc. Natl. Acad. Sci. USA, 1985, 82:2508) and liver cells (Stockert et al., 1980). The asialoglycoprotein receptor of hepatocytes is a particularly active endocytic receptor present on normal hepatocytes having as many as 500,000 surface ligand binding sites per cell (Schwartz et al., J. Biol. Chem. 1981, 256:878). This number is decreased when those cells become cancerous hepatoma cells (Stockert et al., 1980; Schwartz et al. 1981). The number of these receptors on the surface of malignant cells is reduced in number by 60% to 95% depending on the type of tumor. Stockert et al. 1980 reported that primary hepatocellular carcinomas have 37% to 5% of the asialoglycoprotein receptors present on normal cells. Other receptors that are found on normal liver cells include mannose/N-acetylglucosamine receptor cells (Stahl et al., Cell, 1980, 19:207–215) and galactosyl or N-galactosaminyl receptors isolated from liver cell membranes (Stockert et al. 1980). Thus the attachment of a radioprotectant to a carrier that binds the asialoglycoprotein receptor provides a novel method for selectively delivering therapeutic amounts of radioprotectant to normal liver cells, in particular the normal hepatocytes within the liver.

The radioprotectants in accordance with a preferred embodiment of the invention are made by forming a complex between a radioprotective compound (see Table 1 for examples of chemoactive radioprotective compounds (CRC)) and a carrier (Tables 1 and 2 for RME specific carriers). Specific embodiments may include carriers that are polysaccharides, glycoproteins, neoglycoproteins, lipoproteins or proteins. The terminal glycoside of the glycoprotein, neoglycoprotein or polysaccharide has an important effect on the binding affinity of the carrier for the membrane receptor. Examples of suitable terminal glycosides include mannose, galactose, arabinose or rhamnose. Where polysaccharides are the carrier of choice, these may include arabinogalactan, mannan or fucoidan. Other carriers include any of the degradation products or derivatives of arabinogalactan, mannan or fucoidan. Complex formation is achieved by attachment of the CRC to the carrier through either covalent bonds (as shown in Examples 1, 3, and 4) or non-covalent bonds (as shown in Example 2). The carrier provides a means for directing radioprotectants to cells whose protection is desired (non-target normal cells) by recognizing and binding cell surface receptors while at the same time directing the radioprotectant away from those cells whose destruction is desired (cancer cells).

The choice of the radioprotective agent depends on its ability to be complexed to the carrier and its effectiveness at protecting the non-target normal cells from radiation during treatment of malignant cells. In specific embodiments of this invention, examples of chemoactive radioprotective compounds (CRC) have been selected to demonstrate the method of obtaining radioprotection of non-target cells. Examples of radioprotectant agents that are suitable for delivery to non-target cells using carriers include antioxidants, enzymes, cationic thiols, sulfhydryl compounds and free radical scavengers.

Figure 1:
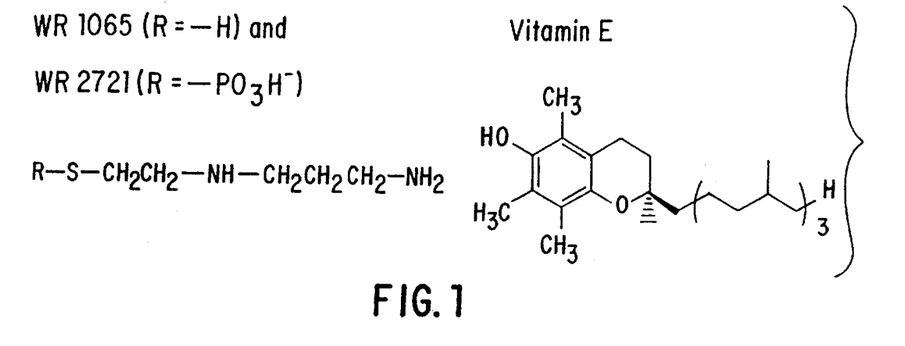
FIG. 1 shows the structure of three radioprotectants; WR 2721, WR 1065, and vitamin E.

The structure of two radioprotectants: a cationic thiol, WR 2721 (S-2-(3-aminopropylamino) ethyl phosphorothioate) and a hydroxyl-aryl compound, Vitamin E are illustrated in FIG. 1. These molecules have previously been demonstrated to have good chemoactive radioprotectant activity (Patchen et al., 7th International Conference on Chemical Modifiers of Cancer Treatment, Clearwater, Fla., 1991) but lack either cell or organ specificity.

Figure 2:
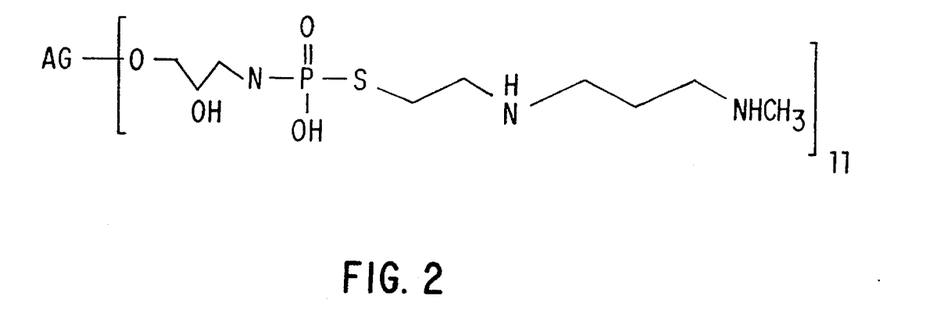
FIG. 2 shows a radioprotectant, WR 3689 coupled to the carrier arabinogalactan.

CRC molecules such as WR 2721 or Vitamin E can be coupled to carriers according to the invention. As depicted in FIG. 2, WR 3689 (an N-methylated analog of WR 2721) is covalently bound to a carrier (an amine derivative of arabinogalactan) through a phosphate-amine linkage by the method described in Example 1. This CRC-carrier complex can then be administered in vivo and a biological effect observed as described in Examples 5 and 6.

Thus, the attachment of a CRC to a carrier binding the asialoglycoprotein receptor results in the delivery of the CRC to the liver generally and specifically to healthy hepatocytes within the liver.

Figure 3:
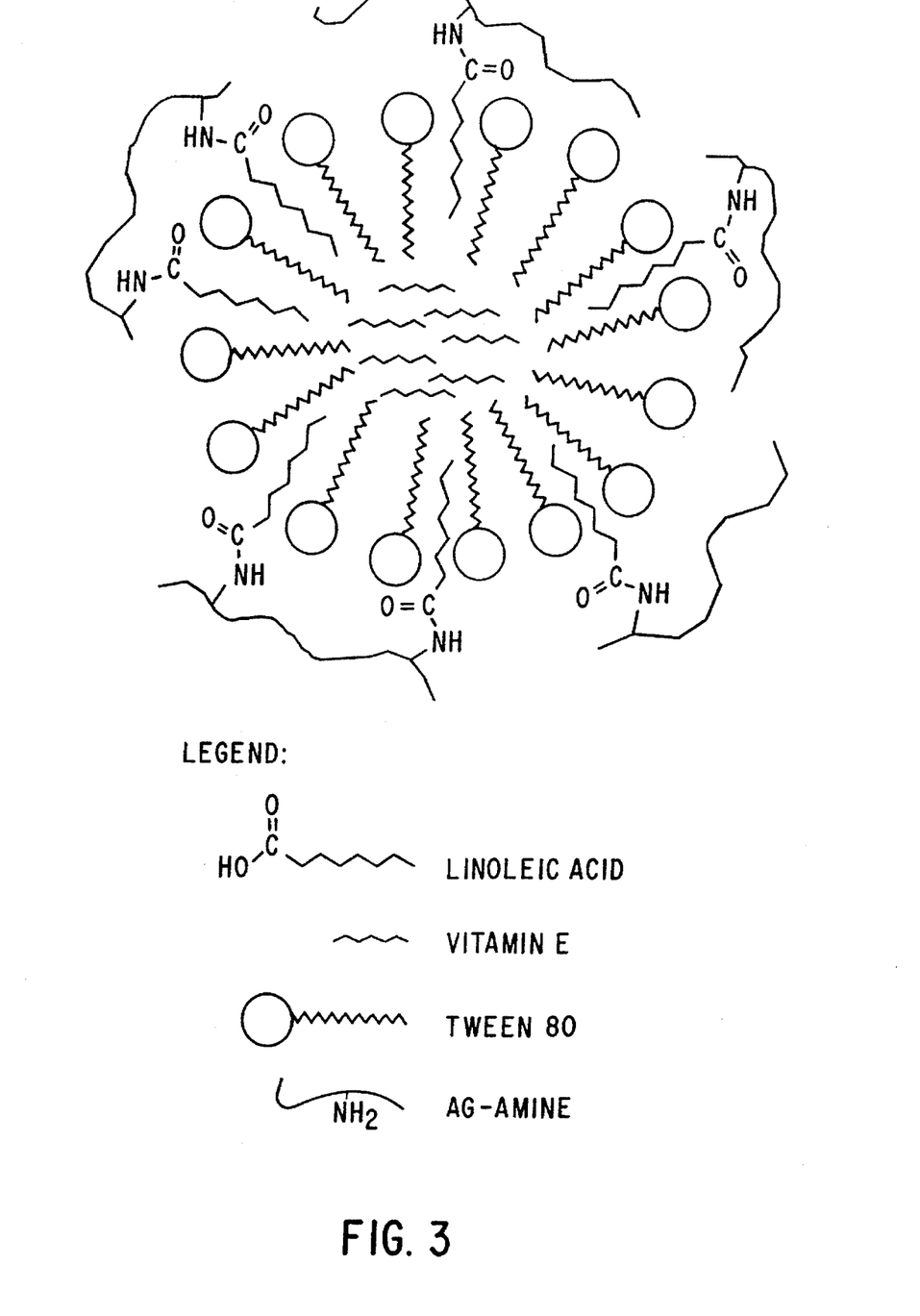
FIG. 3 is a radioprotectant Vitamin E coupled to the arabinogalactan carrier as a micelle.

FIG. 3 illustrates how the carrier arabinogalactan can be associated with CRC-vitamin E contained within a micelle. This association may occur in a number of ways including the adsorption of the carrier to the micelle, and the reaction of the carrier with chemical groups exposed on the surface of the micelle. As shown in FIG. 3, a micelle is an aggregate of a number of ampiphilic molecules about 5–800 nm in size in which the hydrophilic portions are aligned toward water molecules and the hydrophobic regions are aligned toward water insoluble molecules. This arrangement provides a method of delivering chemoactive radioprotectant compounds that are water insoluble or are difficult to chemically modify for attachment to carriers. Micelles offer the opportunity to increase the ratio of chemoactive radioprotectant compounds to carrier without sacrificing bioactivity of the carrier. Accordingly, a micelle permits the delivery of a greater number of CRCs than is possible with an inert carrier and decreases the chances for potential toxicity associated with the carrier. Since the carrier completely encapsulates the CRC, the cells of the body are not exposed to the CRC until the micelle is internalized and degraded within a cell. In the Example 2, arabinogalactan provides receptor recognition for the shielded vitamin E.

Vitamin E (alpha-tocopherol) is recognized to be an effective radioprotectant. According to specific embodiments of this invention, alpha-tocopherol is conjugated to proteins selected as carriers, the proteins being ovalbumin (Example 3) and transferrin (Example 4) and complexed to a polysaccharide, arabinogalactan (Example 2), although polysaccharide conjugates can also be produced. Administration of arabinogalactan-Vitamin E complex to experimental mice demonstrate that this complex is substantially more potent than free drug and protects normal bone marrow cells from the effects of radiation (Example 7). Like arabinogalactan, ovalbumin and transferrin are recognized by RME receptors (Table 2) and are expected to have a similar effect to that of arabinogalactan in vivo.

Ovalbumin has a selective affinity for mannose receptors which are found on normal endothelial cells and macrophages present in many tissues including the spleen and the liver. (Wileman et al., Proc. Natl. Acad. Sci. USA, 1986, 83:2501;, Stahl et al., Cell, 1980, 19:207). Just as with asialoglycoprotein receptors, mannose receptors can be used to facilitate the uptake of compounds to normal cells possessing these receptors. Just as with asialoglycoprotein receptors, numbers of mannose receptors are reduced on malignant cells so that when metastatic cancer invades normal tissue, a nucleus of abnormal cells is created that lack the mannose receptors. Thus the attachment of a CRC to a carrier capable of binding the mannose receptor results in the uptake by endothelial cells and macrophages, and in the selective protection of those cells.

The demonstration that a radioprotectant carrier complex can selectively protects normal non-target tissues is provided in Examples 5 and 6. In these examples, CRC (WR 3689) is complexed with arabinogalactan that binds to normal liver tissue. Used in conjunction with radiation therapy to treat cancerous infiltrations of the liver, Example 5 shows that radio protection is achieved. Micronuclei formation is measured as an indication of chromosomal damage resulting from radiation. Protected cells show less micronuclei formation than unprotected cells. However, the radioprotectant-carrier complex of this invention does not protect malignant cells from radiation (Example 6).

In another embodiment, a CRC may be complexed with a carrier that binds to the asialoglycoprotein receptor of the bone marrow. There is evidence for the presence of asialoglycoprotein receptor on these cells, and in a specific embodiment, a CRC-carrier binding the asialoglycoprotein receptor can be used to protect bone marrow (Example 7). This would have value over the current procedure of autologous marrow transplantation where protection of the marrow is achieved by removal prior to irradiation.

In accordance with the present invention, chemoactive radioprotectant compositions are formulated for in vivo administration by placing the CRC-carrier complex in a pharmaceutically acceptable vehicle. An aqueous buffer solution may be used such as phosphate, citrate or bicarbonate in sterile water or physiological saline containing normal blood plasma cations such as calcium, sodium, potassium and magnesium.

The methods and compositions of the invention are useful in the radioprotection of normal non-target cells in tissues such as the bone marrow and the liver during radiation of abnormal cells as further demonstrated by the examples below.

EXAMPLE 1

Preparation of AG-WR 3689

This example explains how the CRC-WR3689 can be complexed with the carrier, arabinogalactan (AG). Carriers with an affinity for asialoglycoprotein receptor include galactose terminated neoglycoproteins as well as polysaccharides like AG and gum arabic.

A. Synthesis of AG-amine.

Ten grams of AG are dissolved in 25 mL $H_2O$ in a 100 mL roundbottom flask with a stir bar. To this is added 4 g $Zn(BF_4)_2$ in 10 mL $H_2O$ followed by 50 mL epibromohydrin. A reflux condenser is connected to the flask with cold water circulating through the jacket. The reaction is heated in a 100°–110° C. oil bath for 105 minutes. The reaction mixture is then diluted with 30 mL of water and extracted three times each with 85 mL butyl acetate. The product, in the aqueous phase, is precipitated by the addition of ice-cold acetone. The precipitate is further purified by ultrafiltration using a YM3 (3000 MWCO) filter. The pure product, AG-bromide, is isolated as a white solid following lyophilization. The yield of AG-bromide is 7 g. AG-bromide (7 g) is mixed with 32 g ethylene-1,2-diamine, and 18 mL of DMF then heated to about 70° C. for 4 hours. After four hours the ethylenediamine is removed by evaporation under vacuum at about 65° C. The remaining liquid is dissolved in 35 mL of water and this solution dialyzed against 1 L water. The pure product is obtained as a white solid after lyophilization. The yield is 6.5 g. Ninhydrin analysis shows that approximately 11 equivalents of amine are present per mole of product.

B. Conjugation of WR3689 to AG-amine.

WR3689 (an N-methylated analog of WR2721) is prepared using the method described by Rasey et al. (Rasey et al., Radiat. Res., 1986, 106:366–79). Six grams of AG-amine and 1 gram of WR3689 are dissolved in 20 mL of water and the pH adjusted to 6.5. To this is added 1 gram of 1-ethyl-(3,4-dimethylaminopropyl)carbodiimide and the mixture stirred at room temperature for 4 hours. The reaction mixture is then purified by ultrafiltration through a YM3 (3000 MWCO) filter, and the product isolated as a white solid after lyophilization. The yield is 6 g. The product has 10 equivalents of WR3689 per mole of AG determined by acid hydrolysis followed by a colorimetric assay for free sulfhydryl using 5,5' bisdithio 2-nitrobenzoic acid (Fahey et al., Int. J. Radiat. Oncol. Biol. Phys., 1985, 11:1193–7).

EXAMPLE 2

Preparation of AG Coated (+) Alpha-tocopherol Micelle

One gram of tween 80/linoleic acid (100 parts to 1 part) and 100 mg of (+) alpha-tocopherol are mixed with 100 mL of phosphate buffered saline to form a 20 nm micelle. The micelle is next reacted with 100 mg of amino derivatized AG and 50 mg of water soluble carbodiimide. The reactants are allowed to react for 120 minutes and are then subjected to extensive ultrafiltration using a 400 mL ultrafiltration cell fitted with a membrane with a nominal exclusion limit of 50,000 for globular proteins. The solution is finally concentrated by ultrafiltration and lyophilized. The product is analyzed by gel filtration, in which the concentration of polysaccharide in the eluate is determined by the anthrone method and Vitamin E by the absorption at 280 nm.

EXAMPLE 3

Preparation of Ovalbumin(+) Alpha-tocopherol Conjugate

This example explains how the radioprotectant-alpha tocopherol can be complexed with the carrier ovalbumin, a carrier for the mannose receptor. Mannose receptors can be found on normal macrophages that recognize mannose terminated macromolecules (Wileman et al., Proc. Nat. Acad. Sci. USA, 1986, 83:2501; Stahl et al., Cell, 1980, 19:207). Macrophages and endothelial cells are normally present in many tissues including the spleen and liver. When metastatic cancer invades, it can create a space of occupying lesions free of this receptor. Thus the attachment of a CRC to a carrier binding the so-called mannose receptor results in the uptake of the CRC-carrier by endothelial cells and macrophages and in the selective protection of those cells.

To 1 mmol of (+) alpha-tocopherol acid succinate dissolved in 10 mL dimethyl formamide, is added (in order): 1.1 mmol triethylamine and 1.1 mmol of ethylchloroformate. The mixture is allowed to react for 15 minutes, and then is added dropwise to 6 g ovalbumin dissolved in 600 mL of one part 0.1M sodium carbonate (pH 9) to one part dimethyl formamide. The reactants are mixed for 120 minutes and are then subjected to extensive ultrafiltration using 400 mL ultrafiltration cell fitted with a membrane with a nominal exclusion limit of 10,000 for globular proteins. After dissolving the product in phosphate buffered saline, the (+)alpha-tocopherol concentration is analyzed by UV absorption and protein concentration is determined by the Bradford method.

EXAMPLE 4

Preparation of Transfertin (+) Alpha-tocopherol Conjugate

The coupling of the carrier transferrin to the CRC(+) alpha tocopherol is another example of a CRC-carrier complex. Transferrin is cleared from the blood by receptor mediated endocytosis via the transferrin receptor (Ward, Invest. Radiol., 1987, 22:74–83).

To 1 mmol of (+)alpha-tocopherol acid succinate dissolved in 10 mL dimethyl formamide, is added (in order): 1.1 mmol of triethylamine and 1.1 mmol of ethylchloroformate. The mixture is allowed to react for 15 minutes, and then is added dropwise to 4 g transferrin dissolved in 600 mL of one part 0.1M sodium carbonate (pH 9) and one part dimethyl formamide. The reactants are mixed for 120 minutes and are then subjected to extensive ultrafiltration using a 400 mL ultrafiltration cell fitted with a membrane with a nominal size exclusion limit of 10,000 for globular proteins. The solution is concentrated by ultrafiltration and lyophilized. After dissolving the product in phosphate buffered saline, the tocopherol concentration is analyzed by UV absorption and the protein concentration is determined by the Bradford method.

EXAMPLE 5

In vivo Demonstration of the Protective Effect of AG-WR 3689

This example demonstrates the radioprotective effect of the invention on normal tissue.

Two groups (three animals per group) of 8–10 week old Sprague-Dawley rats are used. Group 1 animals are treated with 100 mg/kg of AG-WR3689 as produced in Example 1, while Group 2 animals are treated with saline vehicle. One half hour after treatment, each of the animals is subjected to radiation sufficient to produce micronuclei, about 30 Gy ($^{137}$Cesium source). Immediately after irradiation, a partial hepatectomy is performed on each of the animals. After five days recovery, hepatocytes are isolated from the livers of each of the animals, stained with acridine orange and counted for micronuclei. Group 1 animals (AG-WR 3689) contain fewer micronuclei on average than the Group 2 animals (saline). To demonstrate radioprotective effects, both the dose of radiation or the dose of AG-WR 3689 can be adjusted. The former is adjusted to achieve an increase in hepatic micronuclei in the Group 2 animals without undue mortality, the latter is adjusted to maximize the reduction in micronuclei.

EXAMPLE 6

In Vivo Demonstration of the Radioprotective Efficacy in the Radiation Treatment of an Implanted Micrometastases in Rats In this example, the carrier - CRC complex does not protect malignant cells from radiation.

Fifteen rats are inoculated with approximately $5 \times 10^5$ isolated rat mammary carcinoma cells injected directly into the liver at two sites (right and left lobes). After 21 days the number and size of hepatic micrometastases are determined using ferrite-enhanced magnetic resonance imaging. Ten of the rats showed at least 15 micrometastases ranging in size from 1 to 10 mm. These rats are divided into three groups. Group 1 (three rats) are treated with 300 mg/kg of AG-WR3689. Groups 2 (three rats) and 3 (four rats) are administered saline. One-half hour after pretreatment, Groups 1 and 2 animals are subjected to radiation at a dosage sufficient to control micrometastases.about 30 Gy ($^{137}$Cesium source). Group 3 animals are not irradiated. Fourteen days after the irradiation, the animals are imaged as before to determine the treatment effect on tumor growth. Animals in Group 1 (pretreated with AG-WR3689 and irradiated) and Group 2 (pretreated with saline and irradiated) show reductions in both number and average size of tumors relative to Group 3 animals. This experiment shows that AG-WR3689 does not protect micrometastases from the cytotoxic effects of radiation.

EXAMPLE 7

Pre-irradiation Treatment of CD1 Mice With AG-Vitamin E Enhances Hemopoietic Reconstitution and Increases Survival This example provides a demonstration that a CRC complexed with a carrier that binds to the asialoglycoprotein receptor of the bone marrow is useful in protecting normal cells in the bone marrow from the harmful effects of radiation.

CD1 mice are divided into two groups (three animals/group). Both Groups are pretreated with 150 mg/kg of asialofetuin in order to block the hepatic uptake of radioprotectant and thereby increase the efficiency of uptake by bone marrow. One-half hour after asialofetuin administration, Group 1 animals receive a dose of 400 mg/kg of AG-Vitamin E as produced in Example 2; Group 2 animals receive saline. After two hours, animals are subjected to whole body irradiation with a dose sufficient to kill hemopoietic cells—about 30 Gy ($^{137}$Cesium source). Two weeks after the irradiation, recovery of multipotent hemopoietic stem cells is measured in a 12-day spleen colony forming unit assay (Patchen et al., 1991, pp. 324–325). Animals treated with saline show less colonies per spleen than the animals treated with AG-Vitamin E indicating the protective effect of the AG-Vitamin E on hematopoietic cells. To demonstrate radioprotective effects in other tissues, the dose of radiation or dose of AG-Vitamin E can be adjusted.

Although certain preferred embodiments of the present invention have been described, the spirit and scope of the invention is by no means restricted to the above.

TABLE 1

Examples of Chemoactive Compounds and RKE-Type Carriers

| Chemoactive Radioprotecting Compounds | RME-type Carriers* |
|---|---|
| Sulfhydryl compounds | Galactose or mannose-terminated glycoproteins |
| Cationic thiol compounds | Galactose or mannose-terminated neoglycoproteins |
| Melanins | Mannose-6-Phosphate glycoproteins |
| Cysteamine derivatives | Arabinose-, galactose-, or mannose-terminated polysaccharides |
| Selenium | Low density lipoproteins |
| Hydroxyl-aryl compounds (Vitamin E, alpha-tocopherol) | Transferrin |
| 6-hydroxy-chroman-2 carboxylic acids (Trolox ®) | Interleukin |
| Enzymes (superoxide dismutase) | IgG, IgA, IgE |
| Free radical scavengers | Insulin |
| Antioxidants | Epidermal growth factor Complement (C3b) |

*Adapted from Menz et al., Receptor Mediated Endocytosis Type MRI Contrast Agents, WO 90/01295.

TABLE 2

Carriers Recognized by Receptor Mediated Endocytosis-type Receptors

| Carriers | References to Receptor Interaction |
|---|---|
| Polysaccharides: | |
| Arabinogalactan | Menz, WO 90/1294[1] |
| Mannan | Taylor, 1986[2] |
| Glycoproteins: | Wileman, 1985[3] |
| Asialoorosomucoid | Neutra, 1985[4] |
| Ovalbumin | Magnusson, 1989[5] |
| Transferrin | Ward, 1987[6] |
| Neoblycoproteins: | |

TABLE 2-continued

Carriers Recognized by Receptor Mediated Endocytosis-type Receptors

| Carriers | References to Receptor Interaction |
|---|---|
| Neoglycoalbumin | Jansen, 1991[7] |
| IgG | Rodewald, 1984[8] |
| Proteins: | |
| Insulin | Wileman, 1985[3] |
| Lipoproteins: | |
| LDL | Wileman, 1985[3] |

[1]Menz et al., WO 90/01295, Intern'l. Appln. PCT/US89/03352, Receptor Mediated Endocytosis Type MRI Contrast Agents.
[2]Taylor et al., Mammalian Mannose Binding Proteins, Clin. Sci., 1986, 70:539–546.
[3]Wileman et al., Receptor Mediated Endocytosis, Biochem. J. 1985, 232:1–14.
[4]Neutra et al., Intracellular Transport of Transferrin-and Asialoorosomucoid-Colloidal Gold Conjugated to Lysosomes After Receptor Mediated Endocytosis, J. Histochemistry and Cytochemistry, 1985, 33:1134–1144.
[5]Magnusson et al., Extremely Rapid Endocytosis Mediated by the Mannose Receptor of Sinusoidal Endothelial Rat Liver Cells, Biochem. J. 1989, 257:651–65B.
[6]Ward, The Structure, Function, and Regulation of Transferrin Receptors, Invest. Radiol., 1987, 22:74–83.
[7]Jansen et al., Hepatic Endocytosis of Various Types of Mannose Terminated Albumins, J. Biol. Chem., 1991, 3343–3348.
[8]Rodewald et al., Receptor Mediated Transport of IgG, J. Cell Biol., 1984, 99:159s–164s.

What is claimed is:

1. A method of treating a mixture of cells containing target cells to be destroyed by radiation therapy and non-target cells so as to protect specific non-target cells in the mixture against damage, comprising:

(i) selecting a radioprotectant compound;

(ii) forming a complex of the radioprotectant compound and a carrier wherein the carrier is both (i) a polysaccharide, and (ii) capable of being bound to a receptor mediated endocytosis (RME) receptor, the RME receptor being present on the non-target cells and substantially absent on the target cells; and (iii) administering the complex to the mixture of cells.

2. A method according to claim 1, wherein the radioprotectant is a chemoactive radioprotectant compound.

3. A method according to claim 1, wherein the non-target cells of step (iii) are bone marrow cells.

4. A method according to claim 1, wherein the non-target cells of step (iii) are liver cells.

5. A method according to claim 2, wherein the radioprotectant agents are selected from the group consisting of antioxidants, enzymes, and free radical scavengers.

6. A method according to claim 1, wherein the carrier of step (ii) is selected from the group consisting of arabinogalactan, mannan, and fucoidan.

7. A method according to claim 5, wherein the carrier of step (ii) is selected from the group consisting of arabinogalactan, mannan, and fucoidan.

8. A method according to claim 5, wherein the antioxidants are sulfhydryl compounds.

9. A method according to claim 1, wherein the complex of the radioprotectant and polysaccharide carrier is capable of binding to an asialoglycoprotein receptor.

10. A method according to claim 1, wherein the complex of the radioprotectant and polysaccharide carrier is capable of binding to a mannose receptor.

11. A method according to claim 1, wherein the complex of step (ii) is a micelle comprising the polysaccharide associated with the radioprotecting compound.

12. A method of treating animal subjects having diffuse cancerous infiltrations with radiation comprising:

(i) selecting a polysaccharide carrier capable of interacting with an RME cell receptor;

(ii) modifying the carrier to form a complex with a radioprotectant agent;

(iii) administering to the subject an effective dose of the complex prior to radiation treatment so as to protect non-target cells during subsequent radiation of tissues at doses sufficient to destroy malignant cells.

* * * * *